United States Patent [19]

Becker et al.

[11] Patent Number: 5,627,190

[45] Date of Patent: May 6, 1997

[54] MESO-AZACYCLIC AMIDES OF IMIDAZOPYRIDINE CARBOXYLIC ACIDS AND ANALOGS THEREOF

[75] Inventors: Daniel P. Becker, Glenview; Daniel L. Flynn, Mundelein; Alan E. Moormann, Skokie; Clara I. Villamil, Glenview, all of Ill.

[73] Assignee: G. D. Searle & Co., Chicago, Ill.

[21] Appl. No.: 417,583

[22] Filed: Apr. 6, 1995

Related U.S. Application Data

[62] Division of Ser. No. 140,374, Oct. 21, 1993, Pat. No. 5,430,040, which is a division of Ser. No. 896,273, Jun. 10, 1992, Pat. No. 5,280,029, which is a division of Ser. No. 666,278, Mar. 7, 1991, Pat. No. 5,137,893.

[51] Int. Cl.⁶ .................. A61K 31/44; C07D 471/04; C07D 221/06
[52] U.S. Cl. ............... 514/294; 514/299; 546/94; 546/112; 546/121
[58] Field of Search .................. 546/112, 121, 546/94; 514/299, 294

[56] References Cited

U.S. PATENT DOCUMENTS

| | | | |
|---|---|---|---|
| 4,273,778 | 6/1981 | Hadley et al. | 514/299 |
| 4,336,259 | 6/1982 | Hadley et al. | 514/299 |
| 4,472,413 | 9/1984 | Hadley et al. | 514/304 |
| 4,797,387 | 1/1989 | King | 514/212 |
| 4,797,406 | 1/1989 | Richardson et al. | 514/299 |
| 4,816,453 | 3/1989 | Watts | 514/217 |
| 5,137,893 | 8/1992 | Becker et al. | 514/293 |
| 5,280,029 | 1/1994 | Becker et al. | 514/300 |
| 5,430,040 | 7/1995 | Becker et al. | 514/299 |

FOREIGN PATENT DOCUMENTS

| | | | |
|---|---|---|---|
| 8767121 | 7/1987 | Australia | C07D 451/04 |
| 094742 | 11/1983 | European Pat. Off. | C07D 451/04 |
| 093488 | 11/1983 | European Pat. Off. | C07D 471/08 |
| 189002 | 7/1986 | European Pat. Off. | A61K 31/445 |
| 201165 | 11/1986 | European Pat. Off. | A01K 31/40 |
| 220011 | 4/1987 | European Pat. Off. | A61K 31/435 |
| 230718 | 6/1987 | European Pat. Off. | C08D 211/58 |
| 315390 | 5/1989 | European Pat. Off. | C07D 451/04 |
| 323077 | 7/1989 | European Pat. Off. | C07D 451/04 |
| 2152049 | 7/1985 | United Kingdom . | |
| 2166726 | 5/1986 | United Kingdom | C07D 453/02 |
| 2169292 | 7/1986 | United Kingdom | C07D 451/02 |

OTHER PUBLICATIONS

Fludzinski et al. "Indazoles as Indole Biosters", *J. Med. Chem.*, 1535–7, 1987, 30(9).

*Primary Examiner*—Alan L. Rotman
*Attorney, Agent, or Firm*—Cynthia S. Kovacevic; Roger A. Williams

[57] ABSTRACT

The imidazopyridines containing meso-azacycle side chains as described herein find utility as antagonists of the serotonin 5-HT$_3$ receptor. As such they are useful for the treatment of humans and animals wherein antagonism of 5-HT$_3$ receptors is beneficial. Therapy is indicated for, but not limited to, the treatment of anxiety, psychoses, depression (especially depression accompanied by anxiety), cognitive disorders, substance abuse dependence and/or withdrawal, gastrointestinal motility disturbancies (including esophageal reflux, dyspepsia, irritable bowel syndrome), emesis caused by chemotherapeutic agents, and visceral pain. Additionally, the compounds of the present invention may find utility as enhancers of nasal absorption of bioactive compounds.

2 Claims, No Drawings

MESO-AZACYCLIC AMIDES OF IMIDAZOPYRIDINE CARBOXYLIC ACIDS AND ANALOGS THEREOF

CROSS-REFERENCE

This is a division of application Ser. No. 08/140,374, filed Oct. 21, 1993 now U.S. Pat. No. 5,430,040 which is a division of Ser. No. 07/896,273, filed Jun. 10, 1992 now U.S. Pat. No. 5,280,029, which is a division of Ser. No. 07/666,278 filed Mar. 7, 1991 now U.S. Pat. No. 5,137,893.

BACKGROUND OF THE INVENTION

The invention herein is directed to compounds and a method of treating gastrointestinal motility disorders of a mammal by administering to the mammal in need thereof a therapeutically effective amount of a compound disclosed herein or a pharmaceutically acceptable salt thereof. The method can be practiced to treat gastrointestinal motility disorders such as gastroesophageal reflux, diseases characterized by delayed gastric emptying, ileus, irritable bowel syndrome, and the like. The compounds of the invention are serotonergic 5-HT$_3$ antagonists and as such are useful for the treatment of conditions, for example, such as anxiety, psychoses and depression.

There are classes of compounds known for the treatment of such disorders. For example, azatetracycle compounds are disclosed in co-pending U.S. patent application Ser. No. 07/515,391 filed Apr. 27, 1990, and N-Azabicyclo [3.3.0] octane amides of aromatic acids are disclosed in co-pending application Ser. No. 07/406,205 filed Sep. 11, 1989. Aza-adamantyl compounds are disclosed in U.S. Pat. No. 4,816,453 and are mentioned generically in U.K. Patent 2,152,049A and European application 0189002A2.

Azabicyclic nonanes are disclosed in European Patent application 0094742A2. Additional azabicyclic compounds are disclosed in U.S. Pat. Nos. 4,797,387 and 4,797,406.

Benzamides have been known as 5-HT$_3$ antagonists and as compounds possessing gastrointestinal motility-enhancing properties. Benzamides of the following formula:

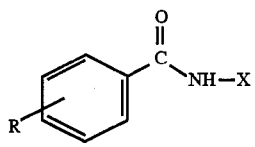

compounds wherein X can be an azabicycloalkane moiety and which exhibit gastrointestinal motility enhancing and/or 5-HT$_3$ antagonist properties are disclosed in EP 0094742A2 and in U.S. Pat. No. 4,797,406. In addition, UK Patent 2,152,049 discloses that certain benzamide derivatives exhibit serotonin M antagonistic activity. Indoleamides of the following formula have also been described as possessing gastrointestinal motility-enhancing and/or 5-HT$_3$ antagonist properties:

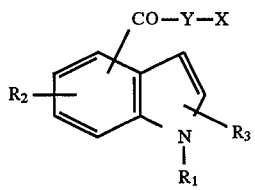

Compounds wherein X contains an aminergic side chain or an azabicycloalkane moiety are described in U.S. Pat. No. 4,797,406.

European patent publication number 0,230,718 discloses certain substituted benzamide derivatives, substituted with piperidinyl analogues as having gastrointestinal motility-enhancing and/or antiemetic activity and/or 5-HT receptor antagonist activity. *J. Heterocyclic Chemistry* (1987) 24:47 describes the preparation of the following compound: No substitution is shown in the phenyl ring and no utility is described.

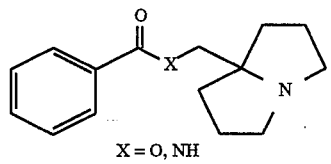

X = O, NH

*J. Pharmaceutical Sciences* (1987) 76:416 describes compounds of generic scope. Utility as anti-arrythmic agents is described.

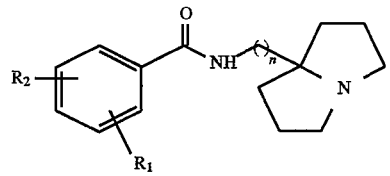

n=1 or 2

R$_1$=H, 2-Me, 4-NH$_2$, 4-OMe, 4-NHCO$_2$Et, 2-OEt, 4-OEt, 3- or 4-NMe$_2$, 3- or 4-NO$_2$; R$_2$=H or 6-Me.

JP Patent 58083694 A2 and JP 0027355B describe anti-arrythmic agents of the following formula wherein n=1 or 2; R$_1$ or R$_2$ are both Me or R$_1$ is H while R$_2$ is nitro, di-lower alkylamino, lower alkoxycarbonylamino, or ethoxy.

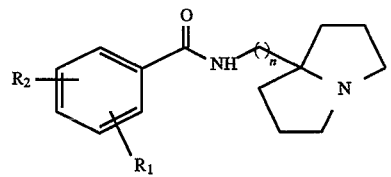

EP Patent 39,903 and U.S. Pat. No. 4,617,401 describe compounds of the following formula wherein X is NH or O and R is H, OMe, OH, or NH$_2$ and Z is a lone electron pair or optionally substituted alkyl group. The compounds are described as spasmolytic, antiarrythmic, and neuromuscular-blocking agents.

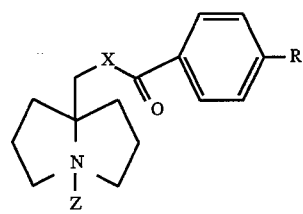

SUMMARY OF THE INVENTION

The compounds of examples 1–8 find utility as antagonists of the serotonin 5-HT$_3$ receptor. As such they are useful for the treatment of humans and animals wherein antagonism of 5-HT$_3$ receptors is beneficial. Therapy is indicated for, but not limited to, the treatment of anxiety, psychoses, depression (especially depression accompanied by anxiety), cognitive disorders, substance abuse dependence and/or withdrawal, gastrointestinal motility disturbancies (including esophageal reflux, dyspepsia, irritable bowel syndrome), emesis caused by chemotherapeutic agents, and visceral pain. Additionally, the compounds of the present invention may find utility as enhancers of nasal absorption of bioactive compounds.

DETAILED DESCRIPTION OF THE INVENTION

The invention herein is directed to compounds of the formula

Ar—CO—X—Z the stereoisomers and pharmaceutically acceptable salts thereof wherein Ar reprsents a radical of the formula.

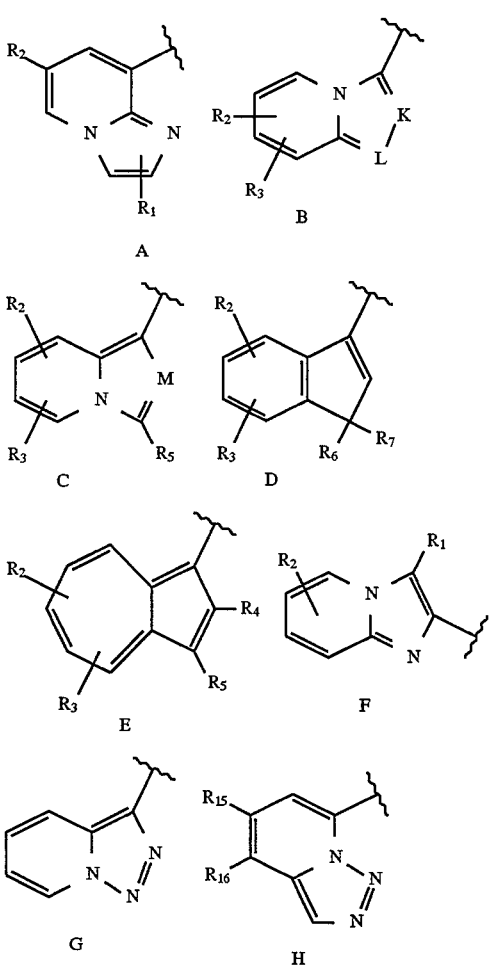

Wherein in Group A, $R_1$ is H, or $C_{1-6}$ alkyl, $R_2$ is H, or halogen;

In Group B, K is N or $CR_4$, L is N or $CR_5$, $R_2$ and $R_3$ are independently H or halogan, $R_4$ is H, or $C_{1-6}$ alkoxy, $R_5$ is H, halogen, $CF_3$, $C_{1-6}$ alkyl, $C_{1-6}$ alkoxy, $C_{1-6}$alkylthio, $C_{1-6}$ alkylsulfonyl, $C_{1-6}$ alkylsulfinyl, $C_{1-7}$ acyl, cyano, $C_{1-6}$ alkoxycarbonyl, $C_{1-7}$ acylamino, hydroxy, nitro, amino, aminocarbonyl, or aminosulfonyl optionally N-substituted by one or two groups selected from $C_{1-6}$ alkyl, $C_{3-8}$ cycloalkyl, and $C_{3-8}$ cycloalkyl$C_{1-4}$alkyl or disubstituted by $C_4$ or $C_5$ polymethylene, phenyl or phenyl $C_{1-4}$ alkyl group optionally substituted in the phenyl ring by one or two of halogen, $C_{1-6}$ alkoxy or $C_{1-6}$ alkyl groups;

In Group C, M is N or $CR_4$, $R_2$ and $R_3$ are independently H or halogen, $R_4$ is H or $C_{1-6}$ alkoxy, $R_5$ is H, halogen, $CF_3$, $C_{1-6}$ alkyl, $C_{1-6}$ alkoxy, $C_{1-6}$alkylthio, $C_{1-6}$ alkylsulfonyl, $C_{1-6}$ alkylsulfinyl, $C_{1-7}$ acyl, cyano, $C_{1-6}$ alkoxycarbonyl, $C_{1-7}$ acylamino, hydroxy, nitro, amino, aminocarbonyl, or aminosulfonyl optionally N-substituted by one or two groups selected from $C_{1-6}$ alkyl, $C_{3-8}$ cycloalkyl, and $C_{3-8}$ cycloalkyl$C_{1-4}$alkyl or disubstituted by $C_4$ or $C_5$ polymethylene, phenyl or phenyl $C_{1-4}$ alkyl group optionally substituted in the phenyl ring by one or two of halogen, $C_{1-6}$ alkoxy or $C_{1-6}$ alkyl groups;

In Group D, one of $R_6$ or $R_7$ is $C_{1-6}$ alkyl and the other is $C_{1-6}$ alkyl, phenyl or phenyl $C_{1-4}$ alkyl optionally substituted in either phenyl ring by one or two of $C_{1-6}$ alkyl, $C_{1-6}$ alkoxy, or halogen, or $R_6$ and $R_7$ together are $C_{2-6}$ polymethylene or $C_{2-5}$ polymethylene interrupted by an —O— linkage, $R_2$ and $R_3$ are independently H or halogen;

In Group E, $R_4$ is H or $C_{1-6}$ alkoxy, $R_5$ is H or $C_{1-6}$ alkoxy, $R_2$ is H, halogen, $CF_3$, $C_{1-6}$ alkyl, $C_{1-6}$ alkoxy, $C_{1-6}$alkylthio, $C_{1-6}$ alkylsulfonyl, $C_{1-6}$ alkylsulfinyl, $C_{1-7}$ acyl, cyano, $C_{1-6}$ alkoxycarbonyl, $C_{1-7}$ acylamino, hydroxy, nitro, amino, aminocarbonyl, or aminosulfonyl, optionally N-substituted by one or two groups selected from $C_{1-6}$ alkyl, $C_{3-8}$ cycloalkyl, and $C_{3-8}$ cycloalkyl$C_{1-4}$alkyl or disubstituted by $C_4$ or $C_5$ polymethylene; phenyl or phenyl $C_{1-4}$ alkyl group optionally substituted in the phenyl ring by one or two of halogen, $C_{1-6}$ alkoxy or $C_{1-6}$ alkyl groups, $R_2$ and $R_3$ are independently H or halogen;

In Group F, $R_1$ is H or $C_{1-6}$ alkyl, $R_2$ is H or halogen; and

In Group H, $R_{15}$ and $R_{16}$ are H or —CH=CH—CH=CH—;

X is NH or O; and

Z represents a radical of the formula

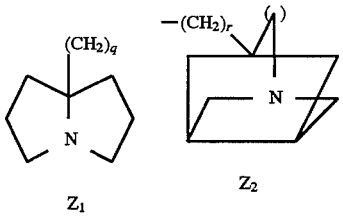

wherein m is 1 or 2, q is 1 or 2, and r is 0 or 1.

The term "cycloalkyl" embraces cyclic radicals having three to about ten ring carbon atoms, preferably three to about six carbon atoms, such as cyclopropyl and cyclobutyl. The terms "alkoxy" and "alkoxyalkyl" embrace linear or branched oxy-containing radicals each having alkyl portions of one to about ten carbon atoms, such as methoxy group.

Specific examples of alkyl groups are methyl, ethyl, n-propyl, isopropyl, n-butyl, sec-butyl, iso-butyl, tert-butyl, n-pentyl, iso-pentyl, methyl-butyl, dimethylbutyl and neopentyl.

Included within the family of compounds of the described are the tautomeric forms of the described compounds, isomeric forms including diastereoisomers and individual enantiomers, and the pharmaceutically-acceptable salts thereof. The term "pharmaceutically-acceptable salts" embraces salts commonly used to form alkali metal salts and to form addition salts of free acids or free bases. Since the compounds contain basic nitrogen atoms, such salts are typically acid addition salts. The phrase "pharmaceutically-acceptable salts" is intended to embrace alkyl quaternary ammonium salts and n-oxides. The nature of the salt is not critical, provided that it is pharmaceutically acceptable, and acids which may be employed to form such salts are, of course, well known to those skilled in this art. Examples of acids which may be employed to form pharmaceutically acceptable acid addition salts include such inorganic acids as hydrochloric acid, sulfuric acid and phosphoric acid, and such organic acids as maleic acid, succinic acid and citric acid. Other pharmaceutically acceptable salts include salts with alkali metals or alkaline earth metals, such as sodium, potassium, calcium and magnesium, or with organic bases, such as dicyclohexylamine. All of these salts may be prepared by conventional means by reacting, for example, the appropriate acid or base with the corresponding compound of the invention.

The compounds that are the subject of the invention herein can be prepared according to the following reaction schemes.

$Z_1$ is known and is prepared as described by Miyano and coworkers [J. Heterocyclic Chemistry (1987) 24, 47 for q=1; J. Pharmaceutical Sciences (1987), 76, 416 & references sited therein]. $Z_2$ is prepared according to schemes 1, 2, and 3.

Scheme 1 describes the preparation of amino-azacycles $Z_2$. The BOC-amine 1 (U.S. patent application Ser. No. 07/515,391) is deprotected with trifluoroacetic acid and the resulting amine is cyclized intramolecularly with the exo-cyclic olefin by treatment with iodine and potassium iodide in the presence of sodium bicarbonate to yield the bridgehead iodide 2. Treatment of 2 with silver isocyanate affords the bridgehead isocyanate which may be hydrolyzed to give the requisite amine $Z_2$ wherein r=0. Alternatively treatment of 2 with silver cyanide affords the bridgehead nitrile which may be reduced to give the desired aminomethyl-azacycle $Z_2$ wherein r=1.

Scheme 2 illustrates the preparation of $Z_2$ hydroxy azacycles. Hydrolysis of bridgehead iodide 2 affords the desired hydroxy azacycle $Z_2$, wherein r=0. Alternatively treatment of 2 with silver cyanade followed by hydrolysis and reduction gives the desired hydroxymethyl azacycle $Z_2$ . . . wherein r=1.

Scheme 3 illustrates the preparation of ethano-bridged azatricycles ($Z_2$. . . , wherein m=2). The azabicycloketone 3 is converted first to its O-benzyloxime. Removal of the N-BOC protecting group, followed by acylation with chloroacetic anhydride & iodide exchange, affords the intermediate 4. Cyclization under reductive radical-cyclization conditions (Bu$_3$SnH, AIBN) affords the ethano-bridged lactam 5. Reduction with lithium aluminum hydride affords the desired ethano-bridged azatricycle $Z_2$. . . .

SCHEME 1: PREPARATION OF $Z_2$ AMINO-AZACYCLES

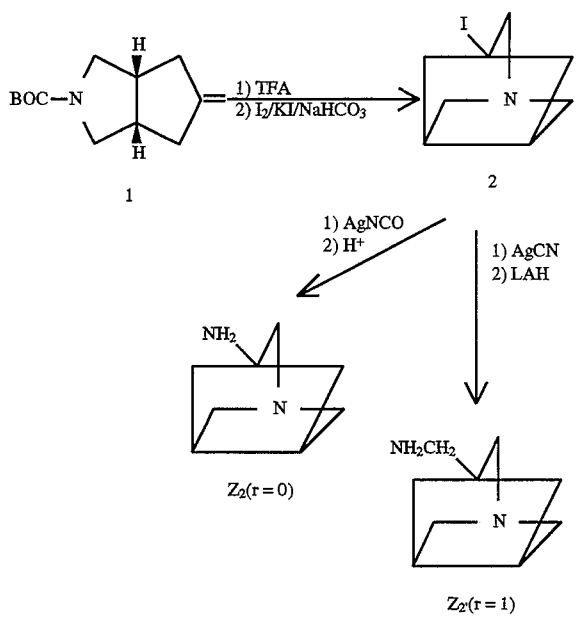

SCHEME 2: PREPARATION OF $Z_2$ HYDROXY AZACYCLES

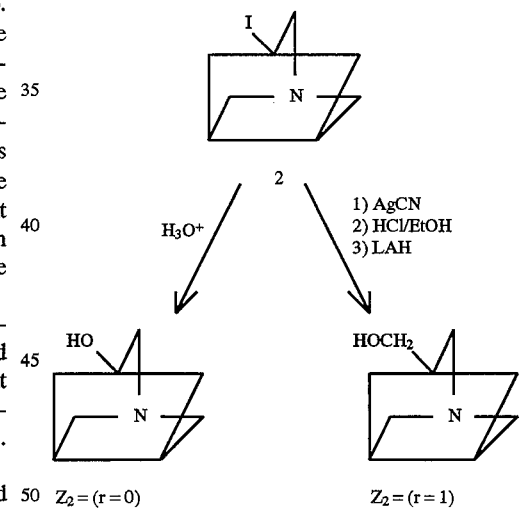

SCHEME 3: PREPARATION OF ETHANO-BRIDGED MESO-AZATRICYCLE

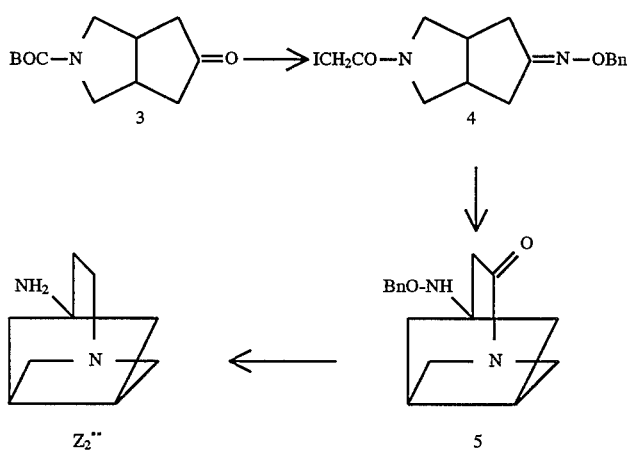

These examples, as well as all examples herein, are given by way of illustration only and are not to be construed as limiting the invention, either in spirit or scope, as many modifications, both in materials and methods, will be apparent from this disclosure to those skilled in the art. In these examples, temperatures are given in degrees Celsius (° C.) and quantities of materials in grams and milliliters unless otherwise noted.

EXPERIMENTALS

EXAMPLE A

Preparation of hexahydro-5-iodo-2,5β-methano-1H-3aα, 6aα-cyclopenta[c]pyrrole

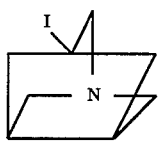

Cis-N-t-butoxycarbonylhexahydro-5-methylenecyclopenta[c]pyrrole [See Co-pending application Ser. No. 07/515,391 filed Apr. 27, 1990] is treated with trifluoroacetic acid to afford an intermediate trifluoroacetate ammonium salt, which is then treated with base and $I_2$ to afford the title compound.

EXAMPLE B

Preparation of tetrahydro-2,5β-methano-1H-3aα, 6aα-cyclopenta[c]pyrrol-5 (3H)-amine

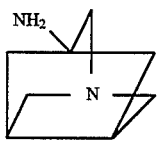

The iodo compound prepared in example A is treated with silver isocyanate to afford the intermediate N-formamide. This formamide is hydrolyzed to give the title compound.

EXAMPLE C

Preparation of tetrahydro-2,5β-methano-1H-3aα, 6aα-cyclopenta[c]pyrrole-5 (3H)-carbonitrile

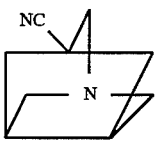

The iodo compound prepared in example A is treated with silver cyanide in dimethylformamide to afford the title compound.

EXAMPLE D

Preparation of tetrahydro-2,5β-methano-1H-3aα, 6aα-cyclopenta[c]pyrrole-5 (3H)-methanamine

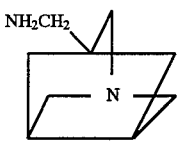

The nitrile compound prepared in example C is reduced with lithium aluminum hydride in etheral solvent to afford the title compound.

EXAMPLE E

Preparation of tetrahydro-2,5β-methano-1H-3aα, 6aα-cyclopenta[c]pyrrole-5 (3H)-methanol

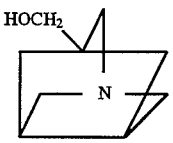

The nitrile compound prepared in example C is converted to the intermediate ethyl ester by treatment with aqueous ethanolic HCl. The ethyl ester is then treated with lithium aluminum hydride in etheral solvent to afford the title compound.

EXAMPLE F

Preparation of 1,1-dimethylethyl hexahydro-5-[(phenylmethoxy)imino]cyclopenta[c]pyrrole-2 (1H)-carboxylate

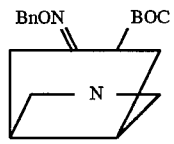

Cis-N-Butoxycarbonylhexahydro-5-oxo-cyclopenta[c]pyrrole is reacted with O-benzylhydroxylamine hydrochloride and sodium acetate in methanol to afford the title compound.

EXAMPLE G

Preparation of octahydro-2-(iodoacetyl)-5-[(phenylmethoxy)imino]cyclopenta[c]pyrrole

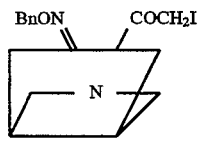

The title compound of example F is treated with trifluoroacetic acid in methylene chloride at room temperature. The volatiles are removed under reduced pressure to afford a residue which is treated with chloroacetic anhydride and triethylamine. The chloroacetylated material is then reacted with NaI in acetone to give the title compound.

EXAMPLE H

Preparation of hexahydro-5-[(phenylmethoxy)amino]-2,5β-ethano-1H-3aα, 6aα-cyclopenta[c]pyrrol-7-one

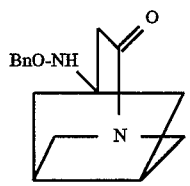

The title compound of example G is treated with tri-n-butylstannane in benzene at reflux containing a catalytic amount of AIBN. Upon workup the title compound is isolated.

EXAMPLE J

Preparation of tetrahydro-2,5β-ethano-1H-3aα, 6aα-cyclopenta[c]pyrrol-5 (3H)-amine

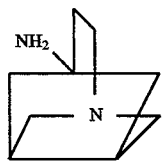

The title compound of example H is reacted with lithium aluminum hydride in tetrahydrofuran to afford after workup the title compound.

EXAMPLE 1

Preparation of 6-chloro-N-(tetrahydro-1H-pyrrolizin-7a (5H)-ylmethyl)imidazo[1,2-a]pyridine-8-carboxamide

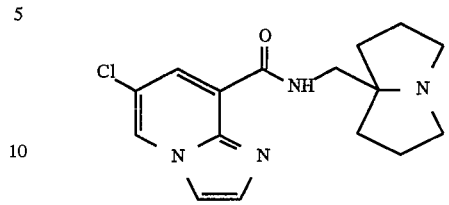

6-chloroimidazo[1,2-a]pyridine-8-carboxylic acid is reacted with carbonyldiimidazole in dimethylformamide and subsequently with 7a-aminomethylhexahydro-1H-pyrrolizine to afford the title compound upon workup.

EXAMPLE 2

Preparation of 6-chloro-N-(tetrahydro-2,5β-methano-1H-3aα, 6aα-cyclopenta[c]pyrrol-5 (3H)-yl)imidazo[1,2-a]pyridine-8-carboxamide)

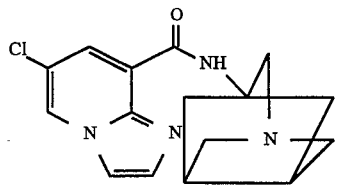

6-Chloroimidazo[1,2-a]pyridine-8-carboxylic acid is reacted with carbonyldiimidazole in dimethylformamide and subsequently with N-hexahydro-1H-2,5β-methano-3aα, 6aα-cyclopenta[c]pyrrol-5β-amine to afford the title compound upon workup.

EXAMPLE 3

Preparation of 3-ethyl-N-(tetrahydro-1H-pyrrolizin-7a (5H)-ylmethyl)indolizine-1-carboxamide

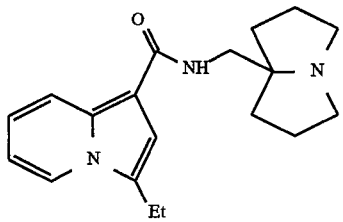

3-Ethylindolizine-1-carboxylic acid is reacted with carbonyldiimidazole in dimethylformamide and subsequently with 7a-aminomethylhexahydro-1H-pyrrolizine to afford the title compound upon workup.

EXAMPLE 4

Preparation of 3-ethyl-N-(tetrahydro-2,5β-methano-1H-3aα, 6aα-cyclopenta[c]pyrrol-5 (3H)-yl)indolizine-1-carboxamide

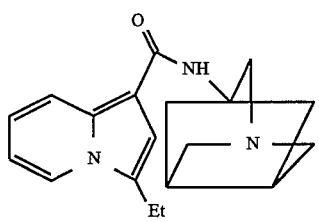

3-Ethylindolizine-1-carboxylic acid is reacted with carbonyldiimidazole in dimethylformamide and subsequently with N-hexahydro-1H-2,5β-methano-3aα,6aα-cyclopenta[c]pyrrol-5α-amine to afford the title compound upon workup.

EXAMPLE 5

Preparation of 3-ethyl-N-(tetrahydro-1H-pyrrolizin-7a (5H)-ylmethyl)imidazo[1,2-a]pyridine-1-carboxamide

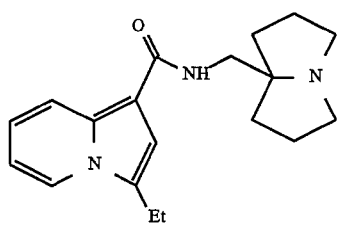

3-Ethylimidazo[1,5-a]pyridine-1-carboxylic acid is reacted with carbonyldiimidazole in dimethylformamide and subsequently with 7 a-aminomethylhexahydro-1H-pyrrolizine to afford the title compound upon workup.

EXAMPLE 6

Preparation of 3-ethyl-N-(tetrahydro-2,5β-methano-1H-3aα, 6aα-cyclopenta[c]pyrrol-5 (3H)-yl)imidazo[1,5-a]pyridine-1-carboxamide

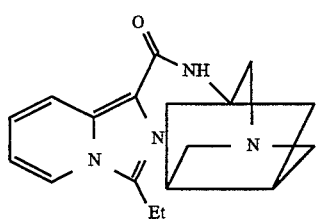

3-Ethylimidazo[1,5-a]pyridine-1-carboxylic acid is reacted with carbonyldiimidazole in dimethylformamide and subsequently with N-hexahydro-1H-2,5β-methano-3aα, 6aα-cyclopenta[c]pyrrol-5α-amine to afford the title compound upon workup.

EXAMPLE 7

Preparation of N-(tetrahydro-1H-pyrrolizin-7a (5H)-ylmethyl)imidazo[1,2-a]pyridine-2-carboxamide

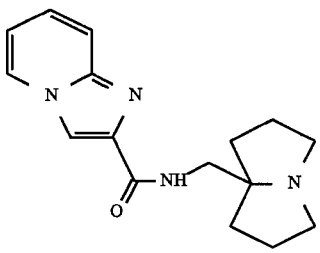

Imidazo[1,2-a]pyridine-2-carboxylic acid is reacted with carbonyldiimidazole in dimethylformamide and subsequently with 7a-aminomethylhexahydro-1H-pyrrolizine to afford the title compound upon workup.

EXAMPLE 8

Preparation of N-(tetrahydro-2,5β-methano-1H-3aα, 6aα-cyclopenta[c]pyrrol-5 (3H)-yl)imidazo[1,2-a]pyridine-2-carboxamide

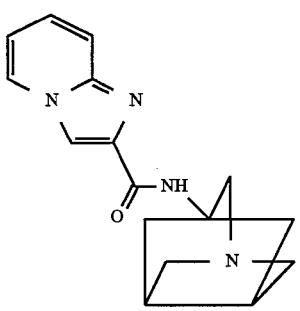

Imidazo[1,2-a]pyridine-2-carboxylic acid is reacted with carbonyldiimidazole in dimethylformamide and subsequently with N-hexahydro-1H-2,5β-methano-3aα, 6aα-cyclopenta[c]pyrrol-5α-amine to afford the title compound upon workup.

The compounds of examples 1–8 find utility as antagonists of the serotonin 5-HT3 receptor. As such they are useful for the treatment of humans and animals wherein antagonism of 5-HT3 receptors is beneficial. Therapy is indicated for, but not limited to, the treatment of anxiety, psychoses, depression (especially depression accompanied by anxiety), cognitive disorders, substance abuse dependence and/or withdrawal, gastrointestinal motility disturbencies (including esophageal reflux, dyspepsia, irritable bowel syndrome), emesis caused by chemotherapeutic agents, and visceral pain. Additionally, the compounds of the present invention may find utility as enhancers of nasal absorption of bioactive compounds.

The compounds herein exhibit 5-HT3 antagonism. 5-HT3 antagonism can be determined by the radioligand receptor binding assay as described herein and in the in vivo Bezold-Jarisch reflex procedure.

Serotonin (5-HT$_3$)

Procedure:

GR65630 binds to the 5-HT$_3$ receptor. Brain cortices are obtained from male rats and a membrane fraction prepared by standard techniques. 0.04 mg of membrane prep is incubated with 0.2 nM [$^3$H]-GR656630 for 60 minutes at 22° C. Non-specific binding is estimated in the presence of 1 uM ICS 205-930. Membranes are filtered and washed 3 times and the filters are counted to determine [$^3$H]-GR65630 specifically bound.*

Results:

$K_d$=2.46 nM

Bmax=154 fmol/mg protein

% Specific Binding: 70

| Effect of Reference Compounds on [H]-GR65630 Bound (0.2 nM) | | | |
|---|---|---|---|
| Compound | $IC_{50}$ | Ki | Hill Coefficient |
| Quipazine | 0.5 nM | 0.18 nM | 0.86 |
| ICS 205-930 | 2.2 nM | 0.51 nM | 1.0 |
| 5-HT | 122 nM | 0.39 uM | 1.0 |
| RU24969 | 320 nM | 1.85 uM | 1.0 |
| Zacopride | 0.55 nM | 0.18 nM | 0.86 |

*Literature Reference:

Kilpatrick G. J., Jones B. J. and Tyers M. B. Identification and distribution of 5-HT$_3$ receptors in rat brain using radioligand binding. Nature, 330:746–748, 1987.

Bezold-Jarisch Reflex

The test sample is administered i.p. (mg/kg) to a group of 3 mice. Thirty minutes later, a 5-HT (0.25 mg/kg i.v.)-induced bradycardia is recorded in pentobarbital anesthetized animals. A greater than 50 percent (>50) reduction in the bradycardic response relative to vehicle-treated control mice is considered significant.

| REFERENCE AGENTS: | Minimum Effective Dose (MED), mg/kg |
|---|---|
| BRL-43694 | 0.05 |
| cisapride | 5 |
| cyproheptadine | 5 |
| domperidone | >10 |
| GR-38032 | 0.5 |
| ketanserin | >10 |
| mecamylamine | 2.5 |
| methysergide | >10 |
| metoclopramide | 5 |
| scopolamine | 2.5 |

This method has been described by Saxena, P. R. and Lawang, A., Arch. Int. Pharmacodyn., 277:235–252, 1985.

Also embraced within this invention is a class of pharmaceutical compositions comprising one or more of the described compounds in association with one or more non-toxic, pharmaceutically acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may with advantage contain an amount of active ingredient from about 1 to 250 mg, preferably from about 25 to 150 mg. A suitable daily dose for a mammal may vary widely depending on the condition of the patient and other factors. However, a dose of from about 0.1 to 3000 mg/kg body weight, particularly from about 1 to 100 mg/kg body weight, may be appropriate.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A compound of the formula

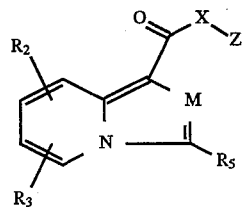

the stereoisomers and pharmaceutically acceptable salts thereof, wherein M is N or $CR_4$, $R_2$ and $R_3$ are independently H or halogen, $R_4$ is H or $C_{1-6}$ alkoxy, $R_5$ is H, halogen, $CF_3$, $C_{1-6}$ alkyl, $C_{1-6}$ alkoxy, $C_{1-6}$ alkylthio, $C_{1-6}$ alkylsulfonyl, $C_{1-6}$ alkylsulfinyl, $C_{1-7}$ acyl, cyano, $C_{1-6}$ alkoxycarbonyl, $C_{1-7}$ acylamino, hydroxy, nitro, amino, aminocarbonyl, or aminosulfonyl optionally N-substituted by one or two groups selected from $C_{1-6}$ alkyl and $C_{3-8}$ cycloalkyl, $C_{1-4}$ alkyl or disubstituted by $C_4$ or $C_5$ polymethylene, phenyl or phenyl $C_{1-4}$ alkyl group optionally substituted on the phenyl ring by one or two of halogen, $C_{1-6}$ alkoxy or $C_{1-6}$ alkyl groups;

X is NH or O; and

Z represents a radical of the formula

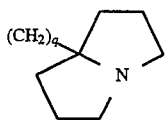

wherein q is 1 or 2.

2. A pharmaceutical composition for the treatment of anxiety, psychoses, depression, gastrointestinal motility disturbances or conditions responsive to 5-HT$_3$ antagonist effect comprising a therapeutically effective amount of a compound as defined in claim 1 and a pharmaceutically acceptable carrier or diluent.

* * * * *